United States Patent
Dolling et al.

[11] Patent Number: 5,468,860
[45] Date of Patent: Nov. 21, 1995

[54] NEW FINASTERIDE PROCESSES

[75] Inventors: Ulf H. Dolling, Westfield; James A. McCauley, Belle Mead; Richard J. Varsolona, Scotch Plains, all of N.J.

[73] Assignee: Merck & Co., Inc., Rahway, N.J.

[21] Appl. No.: 10,734

[22] Filed: Jan. 29, 1993

Related U.S. Application Data

[63] Continuation-in-part of Ser. No. 978,535, Nov. 19, 1992, abandoned.

[51] Int. Cl.⁶ .................................................. C07D 221/04
[52] U.S. Cl. ................................................................ 546/77
[58] Field of Search ................................................. 546/77

[56] References Cited

U.S. PATENT DOCUMENTS

| | | | |
|---|---|---|---|
| 4,760,071 | 7/1988 | Rasmusson et al. | 546/77 |
| 5,061,801 | 10/1991 | Williams et al. | 546/77 |
| 5,084,574 | 1/1993 | Bhattacharya et al. | 546/77 |

FOREIGN PATENT DOCUMENTS

| | | |
|---|---|---|
| 0285383 | 4/1987 | European Pat. Off. . |
| 0462662A2 | 6/1990 | European Pat. Off. . |

OTHER PUBLICATIONS

Merck Index 10th Ed, 1983 p. on213.
Eaton, JACS III pp. 8016–8018 (1989).
Levin, Synth. Comm. vol. 12 No. 13 pp. 989–993 (1982).
Evanseck, et al. J. Am. Chem Sac vol. 107 pp. 2349–2353 (1987).
Bodroux Bull Soc. Chem. France 33, 831–7 (1905).
Bull Soc. Chem. France 35, 519 (1906).
Bull Soc. Chem. France 1, 912 (1907).
Bodroux Compt. Rend. 138, 1427–9 (1904).
Bodroux Compt. Rend. 140, 1108–9 (1905).
Bodroux Compt. Rend. 142, 401–2 (1906).
Bhattachyarya Synthetic Communications 20 (17) pp. 2683–2690 (1990)A.
McCauley AChE Symposium Series, Particle Design via Crystallization, vol. 87, No. 284 (1991), pp. 58–63.

*Primary Examiner*—Donald G. Daus
*Attorney, Agent, or Firm*—Catherine D. Fitch; Carol S. Quagliato; Melvin Winokur

[57] ABSTRACT

Disclosed is a new process for producing finasteride which involves reacting the magnesium halide salt of 17βB-carboalkoxy-4-aza-5α-androst-1-en-3-one with t-butylamino magnesium halide, present in at least a 2:1 molar ratio to the ester, formed from t-butyl amine and an aliphatic/aryl magnesium halide at ambient temperature in an inert organic solvent under an inert atmosphere followed by heating and recovering said product finasteride.

Also disclosed are two polymorphic crystalline Forms I and II of finasteride, and methods of their production.

10 Claims, No Drawings

NEW FINASTERIDE PROCESSES

This is a continuation-in-pan of application 07/978,535, filed Nov. 19, 1992, abandoned Sep. 28, 1993.

BACKGROUND OF THE INVENTION

Finasteride, marketed under the tradename of PROSCAR®, by Merck & Co., Inc. is 17β-(N-tert-butyl carbamoyl)-4-aza-5α-androst-1-en-3-one and is a 5α-reductase inhibitor for use in treating acne, female hirsutism, and particularly benign prostatic hyperplasia. See U.S. Pat. No. 4,760,071 (1988), the entire disclosure of which is incorporated herein by reference.

The synthesis of finasteride in U.S. Pat. No. 4,760,071 involves reacting the 17β-(2-pyridylthio) carboxylate of 4-aza-5α-androst-1-ene-3one with t-butylamine.

A further synthesis of finasteride is described in Synthetic Communications, 30 (17), p. 2683–2690 (1990), the entire disclosure of which is incorporated herein by reference. including the reacting of the 17-acylimidazole of 4-aza-5α-androst-1-en-3-one with t-butylamine.

However, both of these reactions require the use of heterocyclic aromatic amines which are expensive and give rise to environmental safety and toxicity considerations. Both of these intermediates are prepared from the 17β-carboxylic acid.

The Bodroux reaction, described by F. Bodroux in the references, Bull. Soc. Chim. France 33, 831 (1905); 35, 519 (1906); 1, 912 (1907); Compt. Rend. 138, 1427 (1904); 140, 1108 (1905); 142, 401 (1906) discloses the reaction of the magnesium halide salts of amines with esters. However, there is no description or teaching that the reaction can be applied to the reaction of a sterically hindered amine, e.g. t-butyl amine, with a sterically hindered ester such as 1.

What is desired in the an is a method of synthesis of finasteride, which is environmentally safe and non-toxic, and does not utilize an aromatic heterocyclic amine. Preferably, the starting compound could be the 17-beta ester, (1) which would eliminate one step of the process in producing the above heterocyclic intermediates.

SUMMARY OF THE INVENTION

We have discovered that the 17β-carboalkoxy ester of 4-aza-5-alpha-androst-1-en-3-one (1) can be reacted with t-butyl amine together with an aliphatic/aryl magnesium halide reagent, e.g. ethyl magnesium bromide, where the magnesium halide reagent and t-butyl amine are present in at least about 2:1 molar ratios to the ester (1), to produce finasteride (2)in good yield. The reaction between the aliphatic/aryl magnesium halide and t-butylamine produces t-butylamino magnesium halide. One mole of t-butylamino magnesium halide is required for the deprotonation of the ester A-ting lactam thereby solubilizing the steroid, a second mole required for the amidation reaction, and a third mole required for the deprotonation of the newly-formed amide. Alternatively, the ester (1) can be deprotonated with a Grignard reagent separately and then reacted with two (2) moles of t-butylamino magnesium halide to undergo the amidation process.

By this invention, there is provided a process for producing finasteride 2 comprising the steps of:

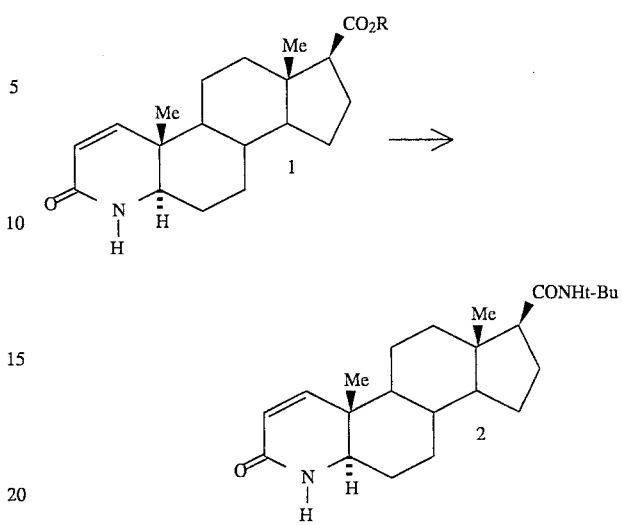

where R is methyl or ethyl, (1) contacting in one vessel the 4-aza-steroid ester 1 with t-butyl amine and aliphatic/aryl magnesium halide in an inert organic solvent under an inert atmosphere at a temperature in the range of –20° to 10° C., stirring the reaction mixture to produce the t-butyl magnesium halide in situ, in at least a 3:1 molar ratio to the ester 1, without reacting the ester with the aliphatic/aryl magnesium halide to form undesired corresponding ketone and alcohol products, (2) heating the reaction to 24° C. to 100° C. to react the ester with the t-butyl amino magnesium halide, and (3) recovering said product finasteride 2 (where tBu indicates tertiary butyl.

Alternatively, the t-butylamino magnesium halide can be first preformed at ambient temperature in the same or separate vessel and then contacted with the 4-aza-steroid ester 1 in at least a 3:1 molar ratio of halide reagent/ester followed by heating to up 100° C. As a further alternative, the t-butyl magnesium halide can be formed in a 2:1 molar ratio to the ester 1, in the same or separate vessel and then contacted with the ester 1, which has been previously contacted with the same or different Grignard reagent in a 1:1 molar ratio to deprotonate and solubilize the ester.

There is additionally provided a method for the synthesis, including separation and crystallization, of multiple, polymorphic crystalline forms of finasteride, as well as the polymorphic forms themselves.

BRIEF DESCRIPTION OF THE INVENTION AND PREFERRED EMBODIMENTS

The starting ester 1 and its synthesis are described in U.S. Pat. No. 4,760,071, the entire disclosure of which is incorporated herein by reference. The compound used to make 1 is the known steroid ester that is saturated at the 1,2 position, which is dehydrogenated with a dehydrogenating agent such as benzeneselenic anhydride in refluxing chlorobenzene.

The preferred starting ester is the compound in which R is defined as methyl. The t-butyl amine and aliphatic/aryl magnesium halide are each used in at least a 3:1 molar ratio to the ester (1) to form a 3:1 molar ratio, and preferably 4:1 to 5:1 molar ratio, of t-butylamino magnesium halide to the ester (1), to ensure proper and complete conversion of 1 to 2 and to minimize impurities. The reaction can be visualized mechanistically as the reaction of 3 moles of t-butylamino magnesium halide, formed by the reaction between the aliphatic/aryl magnesium halide and t-butylamine, with one mole of the ester 1. Alternatively, the reaction can be viewed as 2 moles of t-butyl magnesium halide reacting with one mole of the ester (1) magnesium halide salt. Use of a lithium salt to generate the lithium amide, rather than the magnesium salt of the amide, produces poor results. The aliphatic/aryl magnesium halide is conventional and can be selected where:

(1) the aliphatic/aryl portion is $C_1$–$C_{18}$ linear, branched or cyclic alkyl, e.g. methyl, ethyl, propyl, isopropyl, n-butyl, sec-butyl, t-butyl, hexyl, cyclohexyl, octyl, decyl, dodecyl, tetradecyl, octadecyl, benzyl, allyl, vinyl, ethynyl, and the like; and (2) the aryl portion is phenyl, or mono-, di- or tri-substituted phenyl, wherein the substituents can include $C_1$–$C_4$ alkyl, $C_1$–$C_4$ alkoxy, e.g. methyl, methoxy, fluoro, and the like.

The halide is chloride, bromide or iodide, and preferably bromide. Preferred is ethyl magnesium bromide.

The inert solvent used is a conventional Grignard solvent and can be a $C_4$–$C_8$ linear or cyclic ether, including diethylether, di-n-butyl ether, dimethoxyethane, tetrahydrofuran, dioxane, and the like. The solvent should be dry under the reaction conditions, which are usually carded out under an inert atmosphere, e.g. dry nitrogen, with stirring.

The temperature of the reaction is carded out initially at –20° to 10° C. during:

(1) reaction of t-butylamine and aliphatic/aryl magnesium halide to form the t-butylamino magnesium halide, and (2) the reaction between the ester 1 and t-butyl amino magnesium halide (or Grignard reagent) to form the magnesium halide salt of the ester 1.

Subsequently, the reaction mixture is stirred and generally allowed to warm to room temperature, and then usually heated from 24° C. to 100° C., or up to the boiling point of the solvent to allow the amidation process to proceed. Generally the heating time is 2 to 12 hours.

Alternatively, the t-butylamino magnesium halide may be preformed, for example, at ambient temperature and subsequently reacted with the 4-aza-ester steroid (1) at ambient temperature.

Workup of the crude finasteride is conventional as well as the apparatus used to carry out the process.

In general, chromatography on silica gel and/or recrystallization from a suitable solvent, e.g. methylene chloride/ethyl acetate or acetic acid/water can serve to purify the finasteride.

The order of the addition of ester, t-butyl amine and aliphatic/aryl magnesium halide can be modified and reversed, if desired, with good results. Preferred is where the t-butyl amine is reacted first with the aliphatic/aryl magnesium halide to preform the t-butylamino magnesium halide prior to contacting the ester 1.

The following Example is illustrative of the method claimed herein and should not be construed to represent limitations or restrictions on the scope or spirit of the invention as disclosed.

EXAMPLE 1

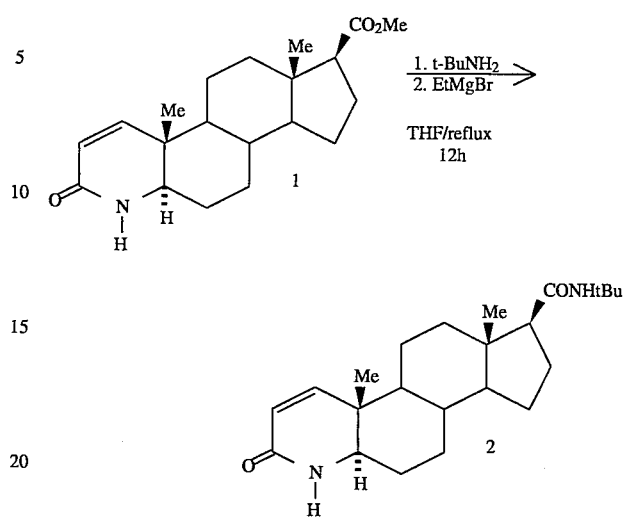

In a flask equipped with an overhead stirrer, a nitrogen inlet, and reflux condenser was placed 840 ml of dry THF and 20.0 g of $\Delta^1$-methyl ester (1). The resulting slurry was cooled to –5° to –10° C., and 27.6 mL of t-butylamine was added. A solution of ethylmagnesium bromide in THF (122 mL, 2M) was added maintaining the temperature of the reaction mixture below 10° C. The reaction was heated at reflux for 12 hours and was added to a cold (10° C.) solution of 25% ammonium chloride in water. The mixture was warmed to 25° C. and allowed to settle. The THF solution was separated and concentrated by atmospheric distillation to 200 mL and the product was crystallized by adding approximately 600 mL of dilute aqueous HCl. The resulting white solid was isolated by filtration and was dried at 70° C. under vacuum to give 21.7 g (97% yield) of finasteride. The product finasteride can be purified by conventional procedures, e.g. recrystallization from methylene chloride/ethyl acetate or acetic acid/water, top. 261° C.

EXAMPLE 2

In a flask equipped with an overhead stirrer, a nitrogen inlet, and reflux condenser was placed 516 mL of dry THF and 27.6 mL of t-butylamine. The solution was cooled to 10° C. and 244 mL of 1M ethylmagnesium bromide in THF was added maintaining the reaction temperature below 30° C. A slurry containing 10.0 g of $\Delta^1$-methyl ester 1 in 100 mL of dry THF was added. The reaction was heated at reflux for 4–6 hours and was added to a cold (10° C.) solution of 25% ammonium chloride in water. The mixture was warmed to 25° C. and allowed to settle. The THF solution was separated and concentrated by atmospheric distillation to 200 mL and the product was crystallized by adding 200 mL of dilute HCl. The resulting white solid was isolated by filtration and was dried at 70° C. under vacuum to give 21.6 g (97% yield) of finasteride.

Polymorphism can be defined as the ability of the same chemical substance to exist in different crystalline structures. The different structures are referred to as polymorphs, polymorphic modifications or forms. finasteride has been found to exist in at least two polymorphic nonsolvated forms, Form I and Form II. The following Examples illustrate methods for obtaining polymorphic Forms I and II of finasteride (Proscar®, MK 906) and some characterization data.

EXAMPLE 3

Finasteride Form I can be prepared by dissolving finasteride in glacial acetic acid (ca. 100 mg/ml) and adding water with stirring until the weight % of water equals or exceeds 84%. The resulting solid phase is collected by filtration and dried under vacuum and at about 50° C. The resulting Form I is characterized by a differential scanning calorimetry (DSC) curve, at heating rate of 20° C./min and in a closed cup, exhibiting a minor endotherm with a peak temperature of about 223° C., an extrapolated onset temperature of about 223° C. with an associated heat of about 11 joules/gin and by a major melting endotherm with a peak temperature of about of 261° C., an extrapolated onset temperature of about 258° C. with an associated heat of about 89 J/gin. The x- ray powder diffraction pattern is characterized by d-spacings of 6.44, 5.69, 5.36, 4.89, 4.55, 4.31, 3.85, 3.59 and 3.14. The FT-IR spectrum shows bands at 3431, 3237, 1692, 1666, 1602 and 688 cm–1. The solubilities in water and cyclohexane at 25° C. are 0.05+0.02 and 0.27+0.05 mg/gm respectively. In addition, Form I of finasteride can be prepared by recrystallization from dry ($H_2O<1$ mg/ml) ethyl acetate and isopropyl acetate. The isolated solids are dried under vacuum at about 50° C. and have the same physical characterization data as given above.

EXAMPLE 4

Form II of finasteride can be prepared by dissolving finasteride in glacial acetic acid (ca. 100 mg/ml) and adding water with stirring until the weight % of water equals about 75% but not in excess of 80%. The resulting solid phase is collected by filtration and dried under vacuum and at about 100° C. The resulting Form II is characterized by a DSC curve, at heating rate of 20° C./min and in a closed cup, exhibiting a single melting endotherm with a peak temperature of about of 261° C., an extrapolated onset temperature of about 258° C. with an associated heat of about 89 J/gin. The x- ray powder diffraction pattern is characterized by d-spacings of 14.09, 10.36, 7.92, 7.18, 6.40, 5.93, 5.66, 5.31, 4.68, 3.90, 3.60 and 3.25. The FT-IR spectrum shows bands at 3441, 3215, 1678, 1654, 1597, 1476 and 752 cm–1. The solubilities in water and cyclohexane at 25° C. are 0.16+0.02 and 0.42+0.05 mg/gm respectively. In addition, Form II of finasteride can be prepared by recrystallization from ethyl acetate containing between 2 to 30 mg/ml of water and isopropyl acetate containing between 2 to 15 mg/ml of water. The isolated solids are dried under vacuum at about 80° C. and have the same physical characterization data as given above. Form II can also be prepared by heating Form I up to about 150° C., holding for about one hour and cooling back to room temperature. The Form II prepared in this manner has the same physical characterization data as given above.

What is claimed is:
1. A process for producing finasteride 2:

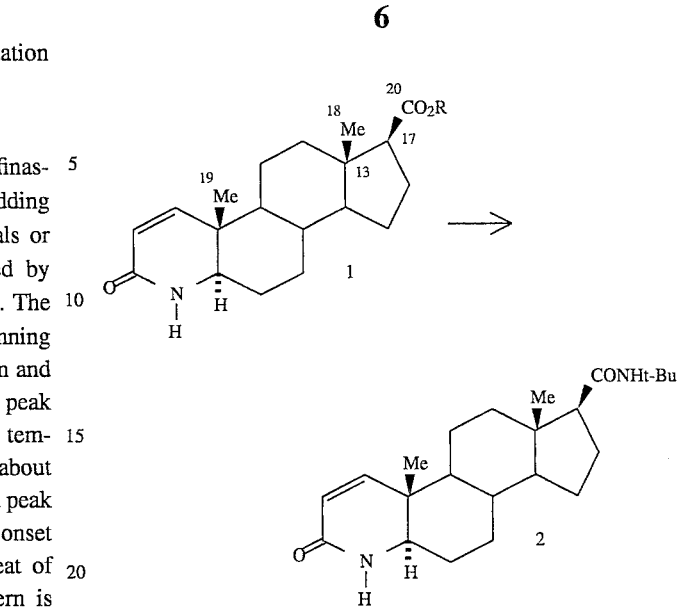

where
R is methyl or ethyl, comprising the steps of
(1) contacting the magnesium halide salt of the 4-aza steroid ester 1 with t-butylamino magnesium halide, wherein the molar ratio of t-butylamino magnesium halide to said ester magnesium halide salt is at least about 2:1, in an inert organic solvent under an inert atmosphere at ambient temperature,
(2) heating the reaction mixture in the range from 25° C. to 100° C., and
(3) recovering said product finasteride 2.
2. The process of claim 1 further comprising the step of reacting t-butylamine and an aliphatic or aryl magnesium halide wherein:
aryl is phenyl, in the range of –20° C. to 10° C. in an inert organic solvent to form said t-butylamino magnesium halide prior to contacting said magnesium halide salt of the ester 1.
3. The process of claim 2 wherein said aliphatic or aryl magnesium halide is an aliphatic magnesium halide wherein the aliphatic moiety is selected from: a methyl, an ethyl, a propyl, an isopropyl, an n-butyl, a sec-butyl, a t-butyl, a hexyl, an octyl, a decyl, a dodecyl, a tetradecyl, an octadecyl, an allyl, a vinyl, an ethynyl, a benzyl or a cyclohexyl radical.
4. The process of claim 3 wherein said aliphatic/aryl magnesium halide is an alkyl magnesium bromide.
5. The process of claim 2 further comprising the step of reacting the ester 1 with an aliphatic or aryl magnesium halide wherein:
aryl is phenyl, in the range of –20° C. to 30° C. in an inert organic solvent to form the magnesium halide salt of the ester 1 prior to contacting said t-butylamino magnesium halide.
6. The process of claim 1 wherein said inert solvent is a $C_4$–$C_8$ linear or cyclic ether.
7. The process of claim 6 wherein said inert organic solvent is diethylether, di-n-butylether, dimethoxyethane, tetrahydrofuran, dioxane.
8. The process of claim 1 wherein R is methyl.
9. The process of claim 1 wherein said molar ratio of t-butylamino magnesium halide to ester 1 is 3:1.
10. The process of claim 1 wherein said molar ratio of t-butylamino magnesium halide to ester 1 is 4–5:1.

* * * * *

UNITED STATES PATENT AND TRADEMARK OFFICE
CERTIFICATE OF CORRECTION

PATENT NO. : 5,468,860
DATED : November 21, 1995
INVENTOR(S) : Ulf H. Dolling

It is certified that error appears in the above-indentified patent and that said Letters Patent is hereby corrected as shown below:

In the Abstract of the invention, at the second line thereof, delete "17βB-car- " and substitute therefor -- 17β-car- --.

Signed and Sealed this

Fourteenth Day of May, 1996

Attest:

BRUCE LEHMAN

Attesting Officer          Commissioner of Patents and Trademarks